United States Patent
Pettinato et al.

(10) Patent No.: US 10,543,863 B2
(45) Date of Patent: Jan. 28, 2020

(54) MOBILE CART FOR AN ORGAN CONTAINER

(71) Applicant: LIFELINE SCIENTIFIC, INC., Itasca, IL (US)

(72) Inventors: David Pettinato, Schaumburg, IL (US); Christopher P. Steinman, Sandy, UT (US); Alan K. Wu, Oak Forest, IL (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 125 days.

(21) Appl. No.: 15/718,724

(22) Filed: Sep. 28, 2017

(65) Prior Publication Data
US 2019/0092364 A1    Mar. 28, 2019

(51) Int. Cl.
*B62B 3/00* (2006.01)
*B62B 3/02* (2006.01)
*A01N 1/02* (2006.01)

(52) U.S. Cl.
CPC ............ *B62B 3/022* (2013.01); *A01N 1/0247* (2013.01); *A01N 1/0273* (2013.01); *B62B 2202/12* (2013.01); *B62B 2205/06* (2013.01); *B62B 2205/20* (2013.01)

(58) Field of Classification Search
CPC . B62B 3/02; B62B 2205/003; B62B 2206/06; B62B 3/00; B66F 7/065
USPC ....................................................... 280/651
See application file for complete search history.

(56) References Cited

U.S. PATENT DOCUMENTS

| | | | | |
|---|---|---|---|---|
| 1,369,944 A | * | 3/1921 | Springer | A47C 4/283 108/118 |
| 3,054,200 A | * | 9/1962 | Steinwedel | D06F 81/04 108/117 |
| 3,345,959 A | * | 10/1967 | Linstead | A47B 3/02 108/119 |
| 4,019,757 A | | 4/1977 | Beger et al. | |

(Continued)

FOREIGN PATENT DOCUMENTS

DE        24 41 870 B1    1/1976

OTHER PUBLICATIONS

U.S. Appl. No. 13/545,598, filed Jul. 10, 2012 in the name of Steinman et al.

(Continued)

*Primary Examiner* — Paul N Dickson
*Assistant Examiner* — Hilary L Johns
(74) *Attorney, Agent, or Firm* — Oliff PLC (57) ABSTRACT

Disclosed is a mobile cart for an organ container. The mobile cart includes a top assembly configured to be releasably secured to the organ container, which is at least one of an organ transporter and an organ perfusion apparatus configured to perfuse an organ. It also includes a support structure attached to the top assembly so as to support the top assembly, the support structure being moveable from an extended position to a collapsed position. The top assembly in turn includes distinct primary and secondary locking mechanisms, each of which is configured to secure the support structure in the extended position. And when the support structure is secured in the extended position, both the primary and secondary locking mechanisms must be actuated for the support structure to be moveable to the collapsed position.

22 Claims, 8 Drawing Sheets

(56) References Cited

U.S. PATENT DOCUMENTS

| | | | |
|---|---|---|---|
| 6,673,594 B1 | 1/2004 | Owen et al. | |
| 7,249,771 B1* | 7/2007 | Brennan | A47J 37/0704 |
| | | | 280/35 |
| 9,119,393 B2 | 9/2015 | Steinman et al. | |
| 9,357,766 B2 | 6/2016 | Steinman et al. | |
| 9,357,767 B2 | 6/2016 | Steinman et al. | |
| 9,402,389 B2* | 8/2016 | Kravitz | A01N 1/0252 |
| 9,565,853 B2 | 2/2017 | Steinman et al. | |
| 10,092,089 B1* | 10/2018 | Yuan | A47B 9/16 |
| 2003/0033672 A1* | 2/2003 | Jehn | A61G 1/0567 |
| | | | 5/611 |
| 2005/0108863 A1* | 5/2005 | Fash | A61G 17/00 |
| | | | 27/2 |
| 2006/0016008 A1* | 1/2006 | Choi | A61G 1/0562 |
| | | | 5/611 |
| 2006/0283669 A1* | 12/2006 | Patten | B66F 7/065 |
| | | | 187/269 |
| 2007/0089648 A1* | 4/2007 | Harrison | A47B 9/16 |
| | | | 108/115 |
| 2007/0275364 A1* | 11/2007 | Hassanein | A01N 1/0247 |
| | | | 435/1.2 |
| 2008/0211206 A1* | 9/2008 | Thorne | B62B 7/068 |
| | | | 280/650 |
| 2009/0165207 A1 | 7/2009 | Reed et al. | |
| 2010/0012909 A1* | 1/2010 | Lee | B66F 7/065 |
| | | | 254/93 R |
| 2012/0276620 A1* | 11/2012 | Kravitz | A01N 1/0236 |
| | | | 435/284.1 |
| 2014/0264207 A1* | 9/2014 | Sekine | B60L 15/20 |
| | | | 254/2 C |

OTHER PUBLICATIONS

U.S. Appl. No. 13/545,281, filed Jul. 10, 2012 in the name of Kravitz et al.
U.S. Appl. No. 13/545,473, filed Jul. 10, 2012 in the name of Kravitz et al.
U.S. Appl. No. 13/545,514, filed Jul. 10, 2012 in the name of Steinman et al.
U.S. Appl. No. 13/097,809, filed Apr. 29, 2011 in the name of Kravitz et al.
H. E. Wang, et al., "Ambulance stretcher adverse events", Quality and Safety in Health Care, vol. 18, No. 3, pp. 213-216, 2009.
Mar. 29, 2019 International Search Report issued in International Patent Application No. PCT/US2018/047726.
Mar. 29, 2019 Written Opinion issued in International Patent Application No. PCT/US2018/047726.

* cited by examiner

MOBILE CART FOR AN ORGAN CONTAINER

BACKGROUND

I. Related Technical Fields

Related technical fields include organ transportation systems and methods, and more specifically, a mobile cart and/or organ container and associated methods for transporting that organ container by way of the mobile cart.

II. Related Art

Advances in organ transplantation and preservation allow for organs to be donated at a location that is far from the recipient of the organ. As such, donated organs must be preserved over an extended time or distance. Organ containers, including portable organ transportation and/or preservation devices such as disclosed in U.S. Pat. No. 6,673,594 to Owen et al., which is hereby incorporated by reference, are known. Other organ containers such as those disclosed in U.S. Pat. Nos. 9,119,393; 9,357,766; 9,357,767; 9,402,389; 9,565,853 and U.S. patent application Ser. Nos. 13/545,281; 13/545,473; 13/545,514; and Ser. No. 13/545,598, the disclosures of which are likewise hereby incorporated by reference, are also known. With such containers, the viability, and thus distance the organ can be transported, can be greatly extended. Such organ containers may be used in the surgical suite where the organ is donated, in transport, and in the surgical suite where the organ is transplanted. Also known are mechanisms by which those organ containers may be transported from location to location. For example, U.S. patent application Ser. No. 13/097,809, which too is hereby incorporated by reference, discloses a type of mobile cart.

SUMMARY

In the aforementioned surgical suites, space is at a premium. Space for every medical device, the surgical team, and the patient must be provided therein. When transporting an organ in an organ container, space must be available in the transporting vehicle, be it an automobile, aircraft, or the like. The organ container must also be readily and securely conveyed between the surgical suite and the transporting vehicle. Each of the locations where the organ container is used has specific needs. For example, it is undesirable for a table or bench to be required specifically for the organ container in the surgical suite because the table or bench would use valuable space and the container could be knocked off of the table or bench. Similarly, it is preferred for the organ container to be conveniently located by the donor or recipient of the organ. Space in the transporting vehicle can be even more precious because the vehicles can be relatively small, especially if the vehicle is an aircraft. Therefore, it is undesirable for the organ container or its transportation mechanism to take up too much precious space in these situations.

Further, although there is a general trend toward smaller organ containers, certain organs, such as livers, are relatively large and may require a larger organ container than smaller organs, such as kidneys. Such relatively larger containers may require a two person lift due to weight or size. The substantial weight or size of these larger organ containers may also require more robust transportation mechanisms and various redundancies during transport to prevent damage to the container or the organ therein caused by, e.g., equipment malfunction or user error. Mechanisms by which these organ containers are transported should be designed with these concerns in mind.

Exemplary implementations of the broad inventive principles described herein thus provide a mobile cart for an organ container that includes a top assembly configured to be releasably secured to the organ container, which is at least one of an organ transporter and an organ perfusion apparatus configured to perfuse an organ. The mobile cart may also include a support structure attached to the top assembly so as to support the top assembly, the support structure being moveable from an extended position to a collapsed position. The top assembly may further include distinct primary and secondary locking mechanisms, each of which is configured to secure the support structure in the extended position. And when the support structure is secured in the extended position, both the primary and secondary locking mechanisms must be actuated for the support structure to be moveable to the collapsed position.

Other exemplary implementations of the broad inventive principles described herein also provide a mobile cart for an organ container that includes a top assembly configured to be releasably secured to an organ container, which is at least one of an organ transporter and an organ perfusion apparatus configured to perfuse an organ. The mobile cart may also include a support structure attached to the top assembly so as to support the top assembly, the support structure being moveable in an extension direction from an extended position to a collapsed position. The top assembly may further include at least one locking mechanism configured to secure the support structure in the extended position. And the support structure may include a damper configured to reduce the speed at which the support structure moves in a descent direction from the extended position to the collapsed position.

Yet other exemplary implementations of the broad inventive principles described herein yet further provide a mobile cart for an organ container that includes a top assembly configured to be releasably secured by way of locks to an organ container, which is at least one of an organ transporter and an organ perfusion apparatus configured to perfuse an organ, the locks being actuated by way of a timed release mechanism that, after disengaging the locks, reengages the locks after a period of time sufficient to remove the organ container from the top assembly. The mobile cart may also include a support structure attached to the top assembly so as to support the top assembly, the support structure including a damper configured to reduce the speed at which the support structure descends to a collapsed position from an extended position. The top assembly may further include (i) a primary locking mechanism configured to secure the support structure in the extended position and actuated by way of a first manipulable portion that is accessible to a user when the organ container is secured to the top assembly, and (ii) a distinct secondary locking mechanism configured to secure the support structure in the extended position and actuated by way of a second manipulable portion that is not accessible to the user when the organ container is secured to the top assembly. And when the support structure is in the extended position, both the primary and secondary locking mechanisms must be actuated for the support structure to be moveable to the collapsed position.

BRIEF DESCRIPTION OF THE DRAWINGS

These and other exemplary implementations can be described with reference to the following figures.

DETAILED DESCRIPTION

Figure 1:
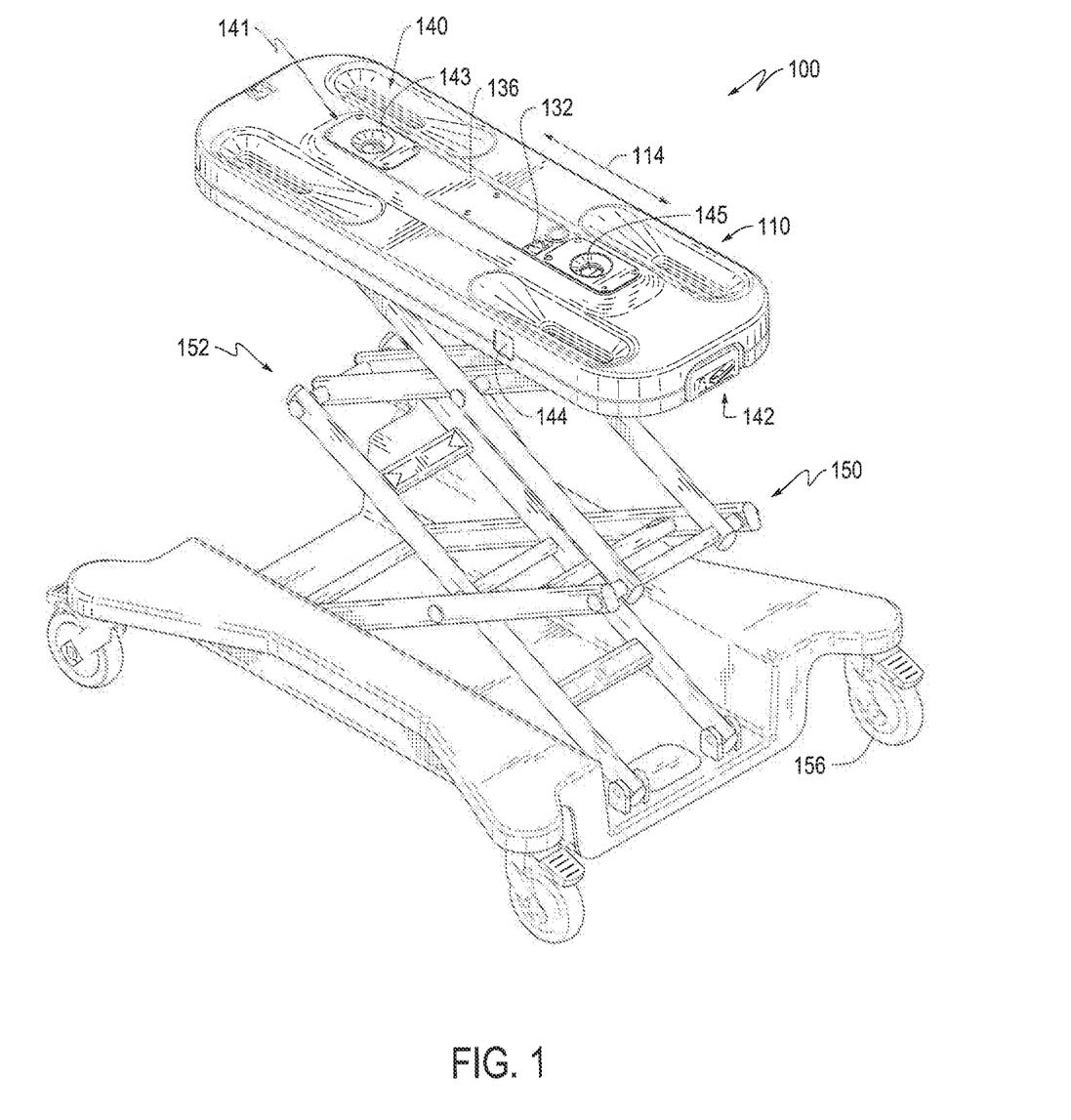
FIG. 1 shows a top perspective view of a mobile cart for a portable organ container when the cart is in an extended position.
Figure 7:
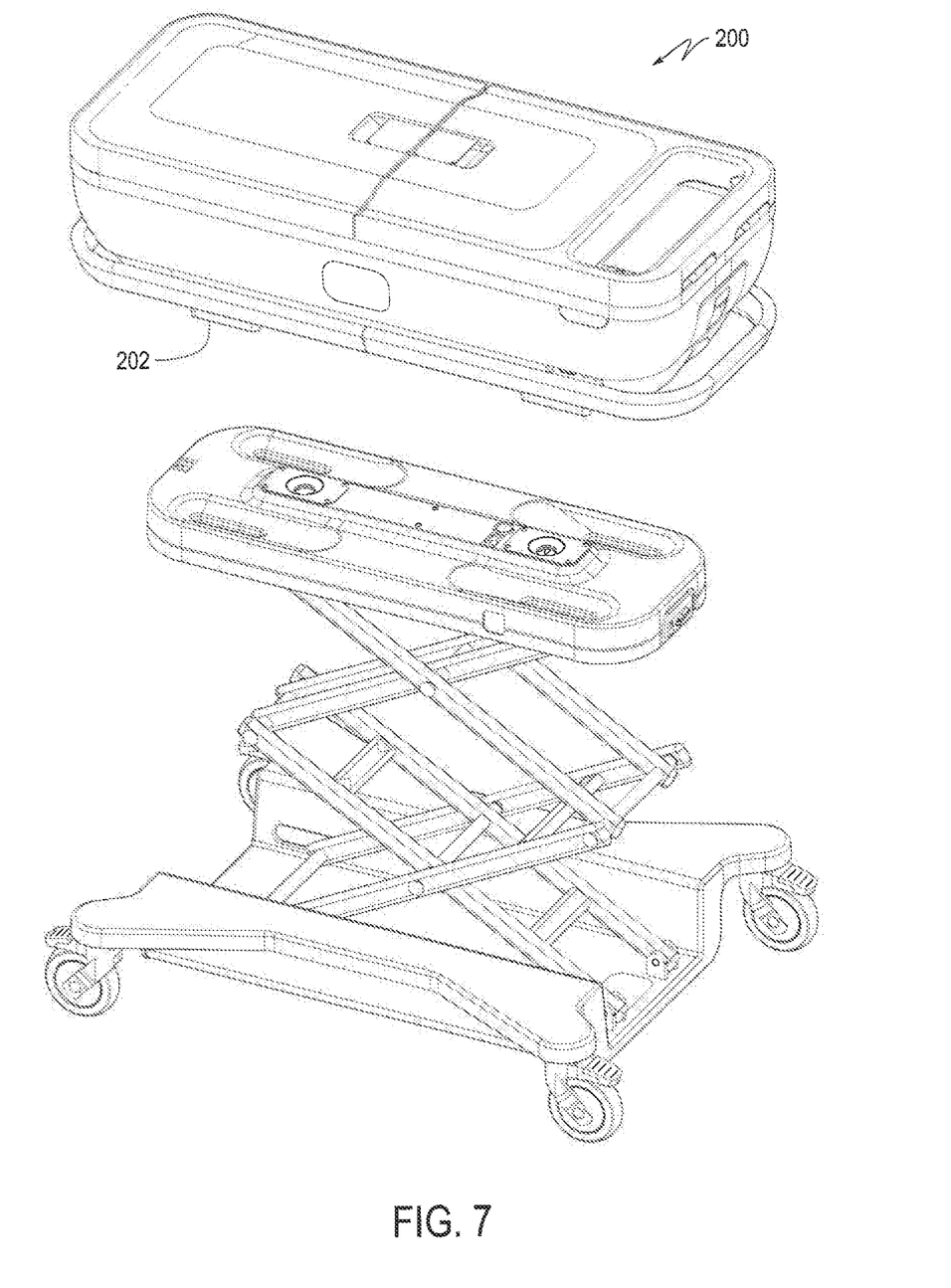
FIG. 7 shows a perspective view of an organ transportation system comprising the mobile cart of FIG. 1 and an organ container.

As previously mentioned, FIG. 1 shows a top perspective view of a mobile cart 100. The mobile cart 100 may include a top assembly 110 for secure attachment to an organ container 200 (shown in FIG. 7), which may be a portable organ preservation device and/or a portable organ perfusion apparatus as disclosed in the above-listed U.S. Patents and Applications.

Figure 2:
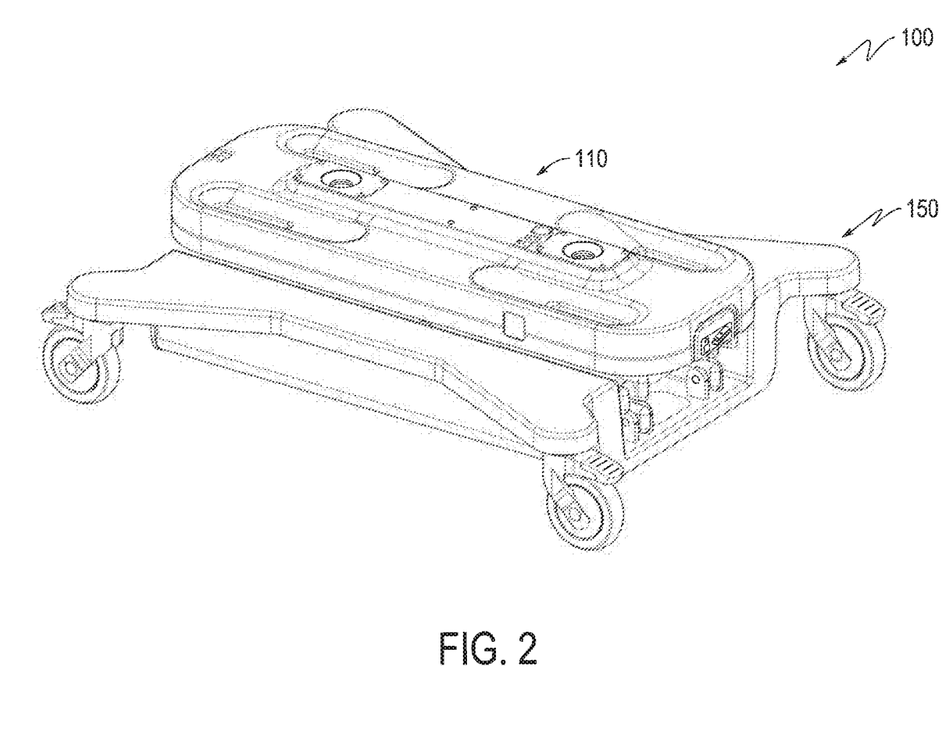
FIG. 2 shows a top perspective view of the mobile cart of FIG. 1 when in a collapsed position.

The mobile cart 100 may also include a support structure 150 comprised of scissor legs 152 attached to the underside of the top assembly 110 to thereby support the top assembly and allow it to be movable in a descent direction from an extended position (FIG. 1), at which the top assembly 110 is supported at its highest position, to a collapsed position (FIG. 2), at which the top assembly 110 is supported at its lowest position. For example, the extended position may be equal to or about 33 inches above the ground on which the support structure 150 rests, and the collapsed position may be equal to or about 12 inches above the ground. It is also conceivable that the extended and collapsed positions may not correspond to the highest and lowest possible positions for the top assembly 110, respectively, but to positions therebetween. And although the top assembly 110 of this example is manually pulled upward by the user from the collapsed to the extended position, and it descends under the force of gravity, other arrangements are considered as being within the scope of the present invention. For example, an electrically or mechanically actuated system can be implemented to automatically control the position of the top assembly 110. The system could be an electronic controller used in conjunction with a geared mechanism. Or this system could use a pneumatic or hydraulic spring mechanism to either extend or collapse the top assembly 110, and it could use a pneumatic or hydraulic logic system, which would eliminate the need for any electronic controllers.

Figure 6:
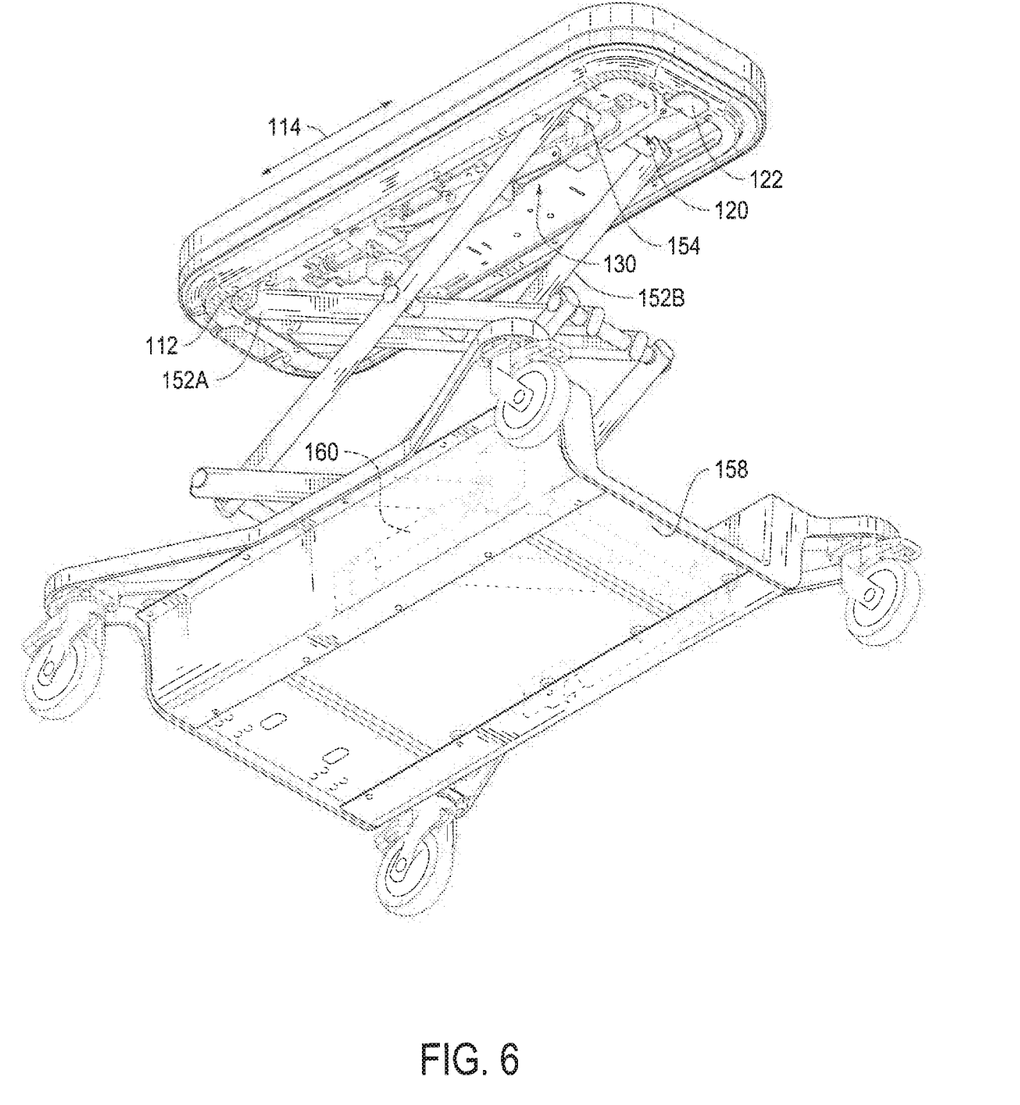
FIG. 6 shows a bottom perspective view of the mobile cart of FIG. 1.

As shown in FIG. 6, one pair of legs 152A of the scissor legs 152 may be secured to the top assembly 110 underside by way of pivot portions 112 such that, during raising and lowering of the top assembly, the legs 152A rotate about the portions 112. On the other hand, ends of the other pair of legs 152B of the scissors legs 152 may be connected together by way of a connecting member or bar 154 that, during raising and lowering of the assembly 110, moves along the longitudinal direction 114 of the top assembly. More specifically, when lowering the top assembly 110 from its extended position, the connecting member or bar 154 moves longitudinally on bearings in a track toward the end of the top assembly 110 at which a first manipulable portion 122 (discussed below) is provided. When raising the top assembly 110 from the collapsed position to its extended position, the connecting member or bar 154 moves in the opposite direction. The connecting member or bar 154 moves in total, either when extending or collapsing, less than 4 inches in the longitudinal direction 114.

Further, the support structure 150 may have wheels 156 on which the mobile cart 100 may roll. These wheels 156 may be removable or otherwise displaceable so that they can be placed in a location that requires less space. This is beneficial in applications where there is limited space for the mobile cart 100 and any attached organ container 200. Preferably, the wheels 156 are lockable to prevent the mobile cart 100 from moving. The support structure 150 is also designed to be rigid. As a result, at least its scissor legs 152 may be made of metal, and particularly aluminum such as Alloy 6063-T6.

Turning back to the top assembly 110, and as also shown in FIG. 6, it may include distinct primary and secondary locking mechanisms 120 and 130 to secure the top assembly 110 in the extended position. Each of these locking mechanisms may likewise be made of metal, and preferably hardened steel, but other suitable materials are also envisioned. The primary locking mechanism 120 may include a hook portion at an end thereof, and it may be biased upward, i.e., toward a topmost surface of the top assembly 110, by a biasing mechanism such as a spring. In use, as the top assembly 110 is actuated by a user, i.e., pulled upward, from the collapsed position of the support structure 150 to the extended position, the longitudinally-moving connecting member or bar 154 is captured and thus secured by the hook portion of the primary locking mechanism 120 to secure the support structure 150 in the extended position. The secondary locking mechanism 130 may likewise include a hook portion at an end thereof, and it may likewise be biased upward toward the top surface of the top assembly 110 by a biasing mechanism such as a spring. In use, as the top assembly 110 is pulled upward from the collapsed position of the support structure 150 to the extended position, the longitudinally-moving connecting member or bar 154 is captured by the hook portion of the secondary locking mechanism 130 to secure the support structure 150 in the extended position. Thus, the locking mechanisms 120, 130 cooperate to automatically secure the support structure 150 in that extended position.

Figure 3:
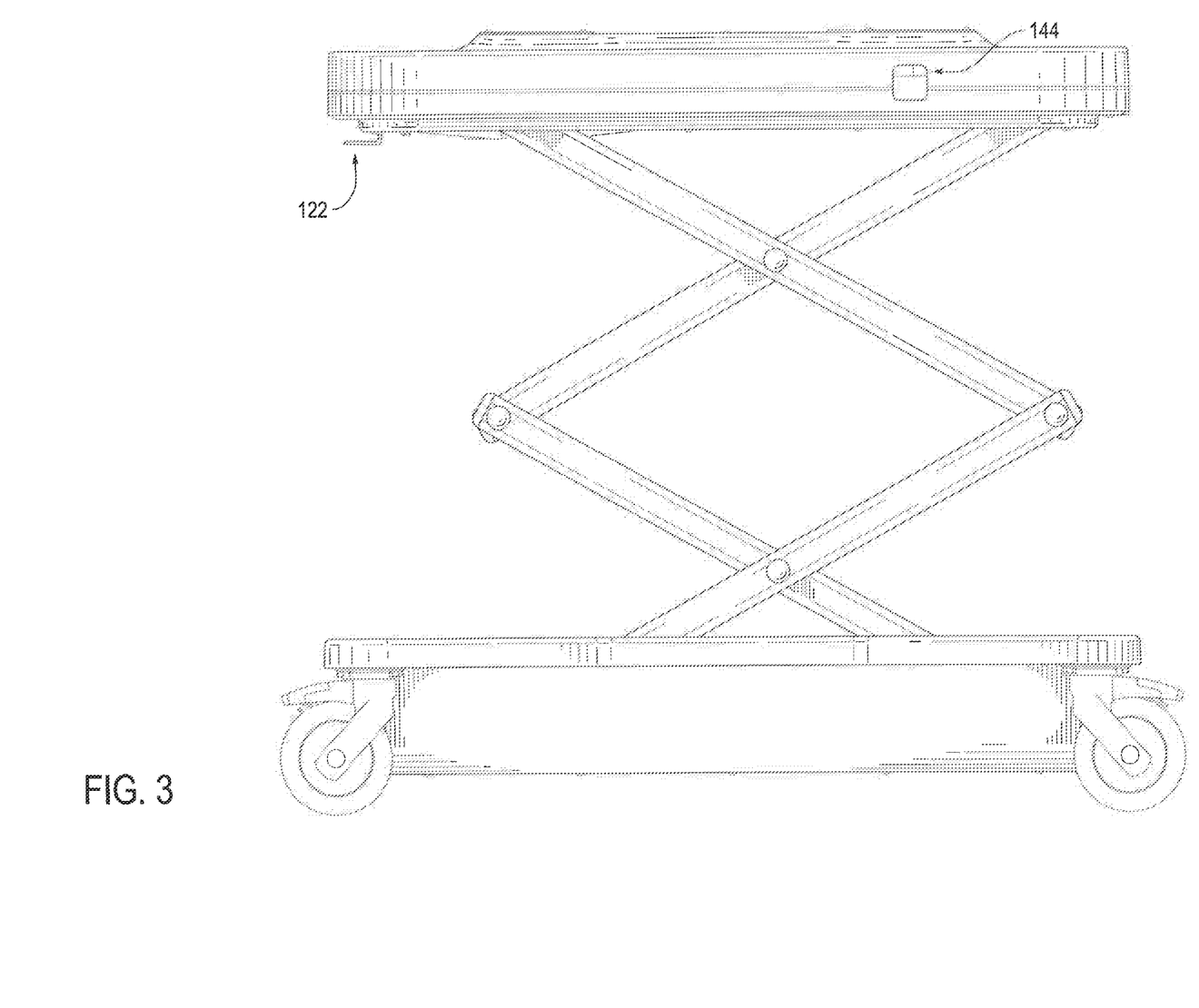
FIG. 3 shows a side view of the mobile cart of FIG. 1.

To disengage them, the primary and secondary locking mechanisms 120, 130 may respectively be actuated by first and second manipulable portions. As shown in FIG. 3, the first manipulable portion 122 may be located so as to be accessible to a user of the mobile cart 100 when the organ container 200 is secured to the top assembly 110. In the specific embodiment shown in FIG. 3, the first manipulable portion 122 is a lever extending from the bottom of the top assembly 110 and then projecting toward a longitudinal end of the top assembly, but other structures are considered to be within the scope of the present invention. As shown in FIG. 6, the first manipulable portion 122 is functionally connected to the primary locking mechanism 120. So to release the connecting member or bar 154 from the primary locking mechanism 120 during the collapsing operation, a user may move the first manipulable portion 122 upward to correspondingly move the primary locking mechanism downward to disengage it and thus to not be in contact with the connecting member or bar.

As shown in FIGS. 1 and 3, contrary to the first manipulable portion 122, the second manipulable portion 132 may be located so as to be inaccessible to a user of the mobile cart 100 when the organ container 200 is secured to the top assembly 110. In the specific embodiment shown in FIGS. 1 and 3, the second manipulable portion 132 is a button located in a central region 136 on a topmost surface of the top assembly 110. As a result, this second manipulable portion 132 may be covered by the bottom of the organ container 200 when it is secured to the top assembly 110, but the portion 132 may be uncovered and accessible when the organ container 200 is removed therefrom. Other structures and arrangements are considered to be within the scope of the present invention, however. As shown in FIG. 6, the second manipulable portion 132 is functionally connected to the secondary locking mechanism 130. So to release the connecting member or bar 154 from the secondary locking mechanism 130 during the collapsing operation, the user may depress the second manipulable portion 132 downward to correspondingly move the secondary locking mechanism downward.

The top assembly 110 may thus advantageously include two locking mechanisms to secure the support structure 150 in the extended position. Although one of the primary and secondary locking mechanisms 120, 130 may be somewhat less sturdy than the other, either is sufficient to maintain the support structure 150 in the extended position alone. A user may thus be required to simultaneously manipulate both manipulable portions 122, 132 to disengage the support structure 150 from the extended position. And because one of those portions, i.e., the manipulable portion 132, may be in a location inaccessible to the user when the organ container 200 is secured to the top assembly 110, this arrangement has the benefit of preventing damage to the container 200 or the organ therein caused by inadvertent collapsing of the support structure 150 with the container 200 still secured. Further, because of the biasing elements and their contacting metal elements, locking of the locking mechanisms 120, 130 to the connecting member or bar 154 may emit a noise, e.g., an audible "click," sufficient to indicate to the user that the support structure 150 is secured in its extended position. This yet further reduces the likelihood of inadvertent collapse of the support structure 150.

The top assembly 110 may also include therein regions 140 for aiding the user to self-center and locate the organ container 200 when placing the container 200 onto the mobile cart 100. These regions 140 may be formed as angled depressions in the topmost surface of the top assembly 110 that correspond to and are configured to receive legs 202 of the container 200.

Figure 4:
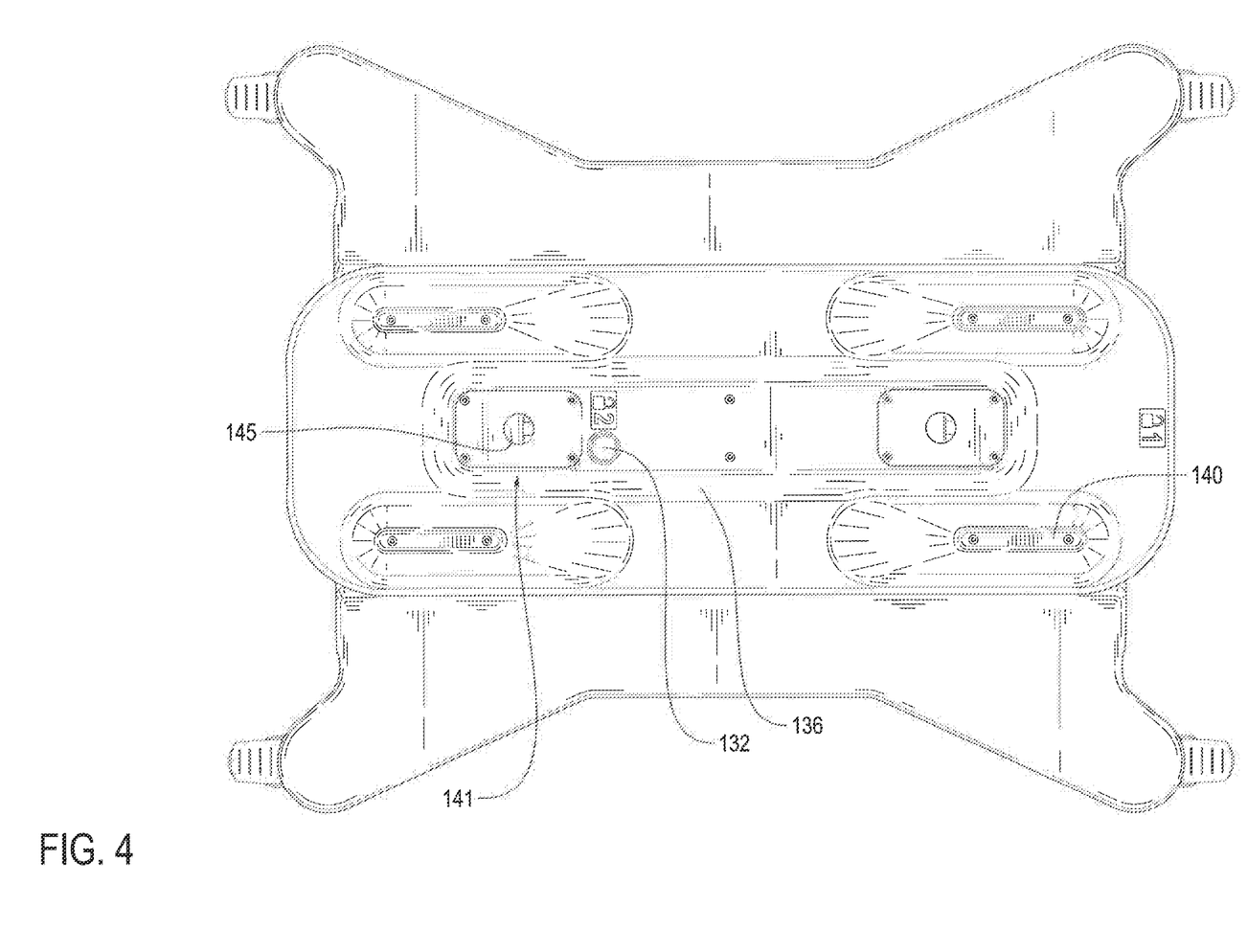
FIG. 4 shows a top view of the mobile cart of FIG. 1.
Figure 8:
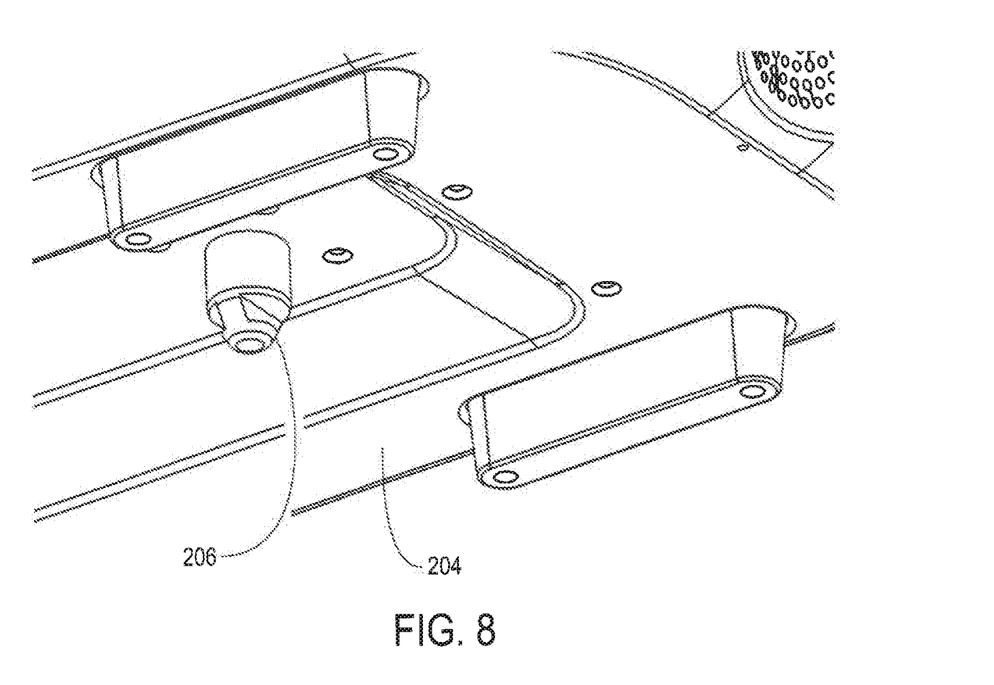
FIG. 8 shows a bottom surface of the organ container of FIG. 7.

As shown in FIGS. 1 and 4, the topmost surface of the top assembly 110 may also include a plurality of locks 141. FIGS. 1 and 4 show two locks 141, but more or fewer are envisioned as being within the scope of the present invention. Each of these locks 141 may comprise a chamfered region 143, and at a center of this region, a hole 145. When the organ container 200 is placed onto the mobile cart 100, the regions 140 may ensure that locking pins 206 projecting from a lower surface 204 of the organ container 200 (shown in FIG. 8) are located in a position to be received by and automatically secured within the holes 145.

Figure 5:
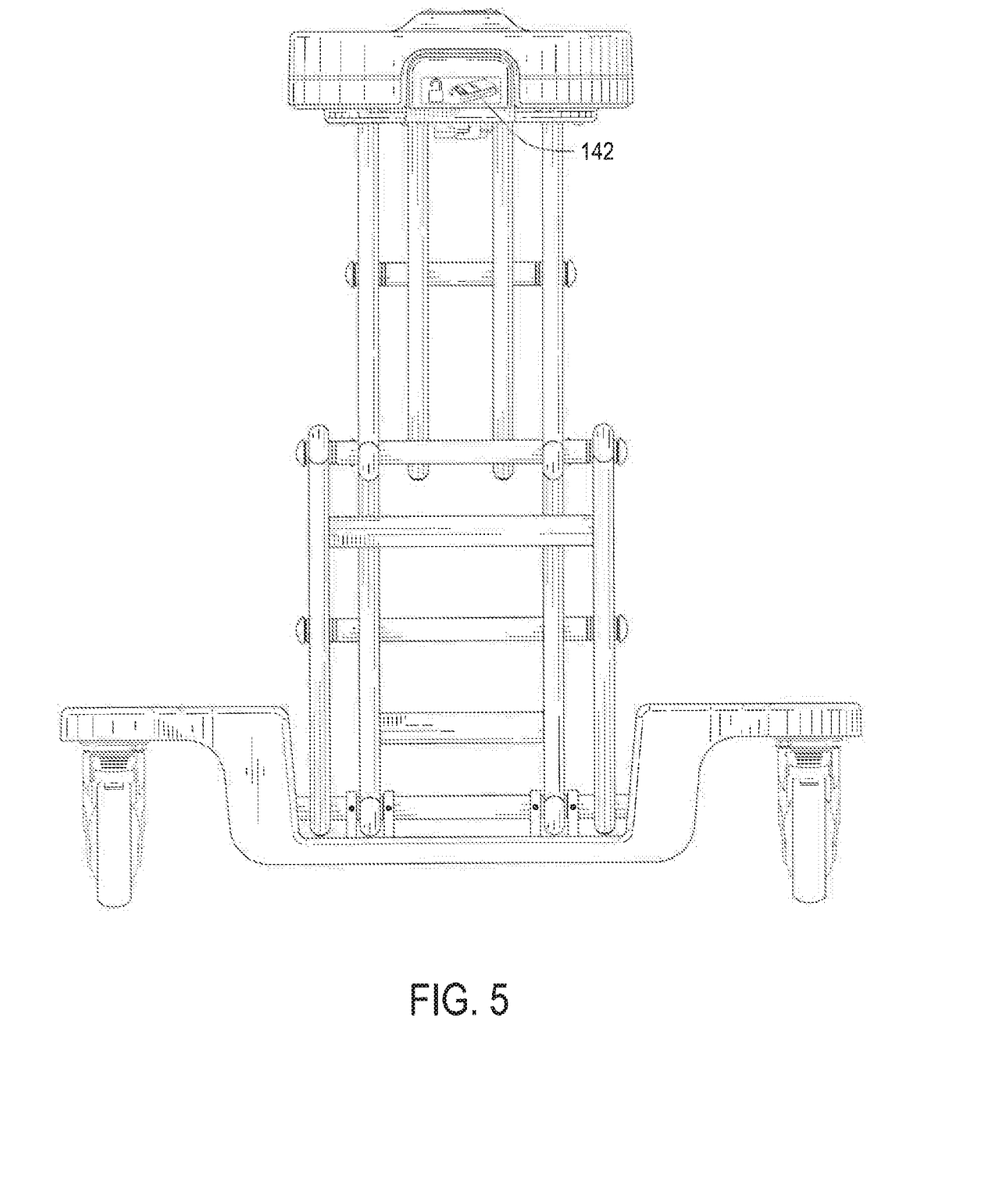
FIG. 5 shows a front view of the mobile cart of FIG. 1.

The locks 141 to secure the organ container 200 may be actuated and released by way of a mechanism 142, shown in FIGS. 1 and 5, and these locks may default to the closed or engaged state by way of a spring biasing mechanism. This release mechanism 142 may be a handle that, when pulled outward away from the top assembly 110, causes the locks 141 to be released. It may also be a timed release mechanism that, after being pulled outward, automatically returns inward to reengage the locks after an amount of time sufficient to allow the user to remove the organ container 200. In other words, the release mechanism 142 may be configured so that the organ container 200 is only removable from the top assembly 110 for a certain period of time after actuation of the release mechanism. For example, the organ container 200 may be removable for about 3 to 10 seconds, and more preferably for about 5 seconds. This arrangement has the benefit of preventing the organ container 200 from resting on the top assembly 110 in an unsecured state, in which the container 200 would be more likely to be knocked over or otherwise displaced from the assembly 110.

The top assembly 110 may also include an indicator 144 that informs the user of the current status of the locks 141 to secure the organ container 200. This indicator 144 may be visual. For example, it may be green when the locks 141 are engaged and the container 200 is thus secured to the top assembly 110, thereby making apparent to the user that it is safe to move the mobile cart 100. The indicator 144 may also turn red when the locks are not engaged, thereby conversely indicating to the user that it is unsafe to move the mobile cart 100. In addition or as alternatives to the red-green visual indicator, other indicators may be employed. For example, the indicator 144 may display text information, e.g., "locked" or "unlocked," to indicate the current status of the locks. Or an audible sound, e.g., buzz or ring, may be emitted during the time period that the locks are disengaged.

In addition to the primary and secondary locking mechanisms 120, 130, the mobile cart 100 may include yet another means by which the organ container 200 secured to the top assembly 110 and organ therein may be protected from uncontrolled, rapid descent from the extended to the collapsed position. In particular, the cart 100 may include a plurality of dampers 160 to slow that descent. One such damper 160 is shown in FIG. 6, and a corresponding damper 160 may be provided on the opposite side of the mobile cart 100. The damper 160 in FIG. 6 is shown as being secured to the base 158 of the support structure 150, but it may be secured elsewhere, e.g., to the top assembly 110. Further, although two dampers 160 are included in the present embodiment, more or fewer dampers are envisioned as being within the scope of the present invention. As shown in FIG. 6, the dampers 160 may be gas springs with pistons that ride on bearings in tracks, but other constructions are possible.

The dampers 160 operate to slow the descent of the top assembly 110, with or without the organ container 200, to a speed that would prevent damage to the organ container 200 or the mobile cart 100 itself. For example, whether loaded with the organ container 200 or with no load, the organ container 200 may descend from the extended position to the collapsed position at a time between 10 to 30 seconds, and preferably of approximately 15 seconds. As a result, even if both the primary and secondary locking mechanisms 120, 130 fail, the top assembly 110 would safely descend to the collapsed position.

While various features have been described in conjunction with the examples outlined above, various alternatives, modifications, variations, and/or improvements of those features and/or examples may be possible. Accordingly, the examples, as set forth above, are intended to be illustrative. Various changes may be made without departing from the broad spirit and scope of the underlying inventive principles.

What is claimed is:

1. A mobile cart for an organ container, comprising:
a top assembly configured to be releasably secured to the organ container, which is at least one of an organ transporter and an organ perfusion apparatus configured to perfuse an organ; and a support structure attached to the top assembly so as to support the top assembly, the support structure being moveable from an extended position to a collapsed position, wherein:
the top assembly includes distinct primary and secondary locking mechanisms, each of which is configured to secure the support structure in the extended position;
a second manipulable portion that actuates the secondary locking mechanism is located at the top assembly so as to be not accessible to a user of the mobile cart when the organ container is secured to the top assembly;
when the support structure is secured in the extended position, both the primary and secondary locking mechanisms must be actuated for the support structure to be moveable to the collapsed position; and
when in the extended position, the support structure is prevented from moving to the collapsed position until the second manipulable portion is manipulated.

2. The mobile cart according to claim 1, wherein the second manipulable portion is a button that is located under the organ container when the organ container is secured to the top assembly.

3. The mobile cart according to claim 2, wherein the button is located in a central region on a topmost surface of the top assembly.

4. The mobile cart according to claim 1, wherein a first manipulable portion that actuates the primary locking mechanism is located at the top assembly so as to be accessible to the user when the organ container is secured to the top assembly.

5. The mobile cart according to claim 4, wherein the first manipulable portion is a lever extending from a bottom of the top assembly.

6. The mobile cart according to claim 4, wherein the primary and secondary locking mechanisms engage with the same member of the support structure to secure the support structure in the extended position.

7. The mobile cart according to claim 6, wherein:
the support structure comprises a plurality of legs; and
the member is a connecting bar that connects at least two of the legs at an upper part thereof.

8. The mobile cart according to claim 1, wherein the organ container is releasably secured to the top assembly by way of locks at the top assembly that are actuated separately from the primary and secondary locking mechanisms.

9. The mobile cart according to claim 8, wherein the locks are actuated by way of a timed release mechanism that, after disengaging the locks, reengages the locks after a period of time sufficient to remove the organ container from the top assembly.

10. The mobile cart according to claim 9, wherein the timed release mechanism comprises a release handle that disengages the locks when pulled outward from the top assembly.

11. The mobile cart according to claim 10, wherein the top assembly includes an indicator that indicates to the user of the mobile cart whether the locks are engaged or disengaged.

12. The mobile cart according to claim 11, wherein the indicator is a visual indicator able to be seen by the user of the mobile cart.

13. The mobile cart according to claim 11, wherein the indicator is an audible indicator able to be heard by the user of the mobile cart.

14. A portable organ transportation system, comprising:
the mobile cart according to claim 1; and
the organ container configured to be secured to the top assembly of the mobile cart so that, when secured, the organ container covers the second manipulable portion.

15. The mobile cart according to claim 1, wherein
the support structure includes a damper configured to reduce the speed at which the support structure moves in a descent direction from the extended position to the collapsed position.

16. The mobile cart according to claim 15, wherein the support structure is configured to allow the top assembly to move in the descent direction at a time between 10 to 30 seconds.

17. The mobile cart according to claim 15, wherein the damper is a gas spring.

18. The mobile cart according to claim 17, wherein:
the support structure is a plurality of legs connecting the top assembly to a base of the mobile cart; and
the gas spring is secured to the base.

19. The mobile cart according to claim 18, wherein the gas spring extends in a direction substantially perpendicular to the descent direction.

20. A portable organ transportation system, comprising:
the mobile cart according to claim 15; and
the organ container configured to be secured to the top assembly of the mobile cart.

21. A mobile cart for an organ container, comprising:
a top assembly configured to be releasably secured by way of locks to an organ container, which is at least one of an organ transporter and an organ perfusion apparatus configured to perfuse an organ, the locks being actuated by way of a timed release mechanism that, after disengaging the locks, reengages the locks after a period of time sufficient to remove the organ container from the top assembly; and
a support structure attached to the top assembly so as to support the top assembly, the support structure including a damper configured to reduce the speed at which the support structure descends to a collapsed position from an extended position, wherein:
the top assembly includes (i) a primary locking mechanism configured to secure the support structure in the extended position and actuated by way of a first manipulable portion that is accessible to a user when the organ container is secured to the top assembly, and (ii) a distinct secondary locking mechanism configured to secure the support structure in the extended position and actuated by way of a second manipulable portion that is not accessible to the user when the organ container is secured to the top assembly, and
when the support structure is in the extended position, both the primary and secondary locking mechanisms must be actuated for the support structure to be moveable to the collapsed position.

22. A portable organ transportation system, comprising:
the mobile cart according to claim 21; and
the organ container configured to be secured to the top assembly of the mobile cart so that, when secured, the organ container covers the second manipulable portion.

* * * * *